(12) United States Patent
Khairkhahan et al.

(10) Patent No.: US 7,862,500 B2
(45) Date of Patent: Jan. 4, 2011

(54) MULTIPLE PARTITIONING DEVICES FOR HEART TREATMENT

(75) Inventors: Alexander Khairkhahan, Palo Alto, CA (US); Serjan D. Nikolic, Los Altos, CA (US); Branislav Radovancevic, Houston, TX (US); Hugh R. Sharkey, Palomar Park, CA (US)

(73) Assignee: CardioKinetix, Inc., Menlo Park, CA (US)

( * ) Notice: Subject to any disclaimer, the term of this patent is extended or adjusted under 35 U.S.C. 154(b) by 1455 days.

(21) Appl. No.: 11/151,156

(22) Filed: Jun. 10, 2005

(65) Prior Publication Data

US 2006/0014998 A1 Jan. 19, 2006

Related U.S. Application Data

(63) Continuation-in-part of application No. 10/302,269, filed on Nov. 22, 2002, now abandoned, and a continuation-in-part of application No. 10/212,033, filed on Aug. 1, 2002, now Pat. No. 7,303,526.

(51) Int. Cl.
*A61N 1/362* (2006.01)
(52) U.S. Cl. .......................................... 600/16; 600/37
(58) Field of Classification Search .................. 600/16, 600/37
See application file for complete search history.

(56) References Cited

U.S. PATENT DOCUMENTS

| | | | |
|---|---|---|---|
| 3,874,388 A * | 4/1975 | King et al. .................. | 606/232 |
| 4,007,743 A | 2/1977 | Blake | |
| 4,425,908 A | 1/1984 | Simon | |
| 4,619,246 A | 10/1986 | Molgaard-Nielsen et al. | |
| 4,685,446 A | 8/1987 | Choy | |
| 4,710,192 A | 12/1987 | Liotta et al. | |
| 4,832,055 A | 5/1989 | Palestrant | |

(Continued)

FOREIGN PATENT DOCUMENTS

WO     WO 00/27292     5/2000

(Continued)

OTHER PUBLICATIONS

Khairkhahan, et al., U.S. Appl. No. 10/436,959, entitled "System for improving cardiac function;" filed May 12, 2003.

(Continued)

*Primary Examiner*—Niketa I Patel
*Assistant Examiner*—Alyssa M Alter
(74) *Attorney, Agent, or Firm*—Shay Glenn LLP

(57) ABSTRACT

This invention is directed to a system and method for partitioning a patient's heart chamber into a productive portion and a non-productive portion which are particularly suitable for treating patients with congestive heart failure. The partitioning system has a plurality of partitioning devices with reinforced, expandable membranes which separate the productive and non-productive portions of the heart chamber. When deployed within the patient's heart chamber, the second partitioning device is off-set from the deployed first partitioning device to cover a region of the wall defining the patient's heart chamber which is not covered by the first partitioning device. The multiple partitioning devices may be independent from each other or may be interconnected, e.g. a tether or strand.

7 Claims, 9 Drawing Sheets

U.S. PATENT DOCUMENTS

| | | | |
|---|---|---|---|
| 4,917,089 A | 4/1990 | Sideris | |
| 5,104,399 A | 4/1992 | Lazarus | |
| 5,192,301 A | 3/1993 | Kamiya et al. | |
| 5,192,314 A | 3/1993 | Daskalakis | |
| 5,375,612 A | 12/1994 | Cottenceau et al. | |
| 5,385,156 A | 1/1995 | Oliva | |
| 5,425,744 A | 6/1995 | Fagan et al. | |
| 5,433,727 A | 7/1995 | Sideris | |
| 5,451,235 A | 9/1995 | Lock et al. | |
| 5,496,277 A | 3/1996 | Termin et al. | |
| 5,527,337 A | 6/1996 | Stack et al. | |
| 5,527,338 A | 6/1996 | Purdy | |
| 5,549,621 A | 8/1996 | Bessler et al. | |
| 5,578,069 A | 11/1996 | Miner, II | |
| 5,634,936 A | 6/1997 | Linden et al. | |
| 5,634,942 A | 6/1997 | Chevillon et al. | |
| 5,702,343 A | 12/1997 | Alferness | |
| 5,709,707 A | 1/1998 | Lock et al. | |
| 5,791,231 A | 8/1998 | Cohn et al. | |
| 5,797,849 A | 8/1998 | Vesely et al. | |
| 5,797,960 A | 8/1998 | Stevens et al. | |
| 5,829,447 A | 11/1998 | Stevens et al. | |
| 5,833,698 A | 11/1998 | Hinchliffe et al. | |
| 5,836,968 A | 11/1998 | Simon et al. | |
| 5,843,170 A | 12/1998 | Ahn | |
| 5,861,003 A | 1/1999 | Latson et al. | |
| 5,865,730 A | 2/1999 | Fox et al. | |
| 5,865,791 A | 2/1999 | Whayne et al. | |
| 5,871,017 A | 2/1999 | Mayer | |
| 5,875,782 A | 3/1999 | Ferrari et al. | |
| 5,876,325 A | 3/1999 | Mizuno et al. | |
| 5,876,449 A | 3/1999 | Starck et al. | |
| 5,879,366 A | 3/1999 | Shaw et al. | |
| 5,882,340 A | 3/1999 | Yoon | |
| 5,910,150 A | 6/1999 | Saadat | |
| 5,916,145 A | 6/1999 | Chu et al. | |
| 5,924,424 A | 7/1999 | Stevens et al. | |
| 5,925,062 A | 7/1999 | Purdy | |
| 5,925,076 A | 7/1999 | Inoue | |
| 5,928,260 A | 7/1999 | Chin et al. | |
| 5,961,440 A | 10/1999 | Schweich, Jr. et al. | |
| 5,961,539 A | 10/1999 | Northrup, III et al. | |
| 5,984,917 A | 11/1999 | Fleischman et al. | |
| 6,024,096 A | 2/2000 | Buckberg | |
| 6,024,756 A | 2/2000 | Huebsch et al. | |
| 6,045,497 A | 4/2000 | Schweich et al. | |
| 6,059,715 A | 5/2000 | Schweich et al. | |
| 6,076,013 A | 6/2000 | Brennan et al. | |
| 6,077,214 A | 6/2000 | Mortier et al. | |
| 6,077,218 A | 6/2000 | Alferness | |
| 6,093,199 A | 7/2000 | Brown et al. | |
| 6,095,968 A | 8/2000 | Snyders | |
| 6,096,347 A | 8/2000 | Geddes et al. | |
| 6,099,832 A | 8/2000 | Mickle et al. | |
| 6,102,887 A | 8/2000 | Altman | |
| 6,125,852 A | 10/2000 | Stevens et al. | |
| 6,132,438 A | 10/2000 | Fleischman et al. | |
| 6,152,144 A | 11/2000 | Lesh et al. | |
| 6,161,543 A | 12/2000 | Cox et al. | |
| 6,193,731 B1 | 2/2001 | Oppelt et al. | |
| 6,221,092 B1 | 4/2001 | Koike et al. | |
| 6,231,561 B1 | 5/2001 | Frazier et al. | |
| 6,258,021 B1 | 7/2001 | Wilk | |
| 6,267,772 B1 | 7/2001 | Mulhauser et al. | |
| 6,290,674 B1 | 9/2001 | Roue et al. | |
| 6,312,446 B1 | 11/2001 | Huebsch et al. | |
| 6,328,727 B1 | 12/2001 | Frazier et al. | |
| 6,334,864 B1 | 1/2002 | Amplatz et al. | |
| 6,343,605 B1 | 2/2002 | Lafontaine | |
| 6,348,068 B1 | 2/2002 | Campbell et al. | |
| 6,355,052 B1 | 3/2002 | Neuss et al. | |
| 6,360,749 B1 | 3/2002 | Jayaraman | |
| 6,364,896 B1 | 4/2002 | Addis | |
| 6,387,042 B1 | 5/2002 | Herrero | |
| 6,406,420 B1 | 6/2002 | McCarthy et al. | |
| 6,419,669 B1 | 7/2002 | Frazier et al. | |
| 6,436,088 B2 | 8/2002 | Frazier et al. | |
| 6,450,171 B1 | 9/2002 | Buckberg et al. | |
| 6,482,228 B1 | 11/2002 | Norred | |
| 6,506,204 B2 | 1/2003 | Mazzocchi | |
| 6,511,496 B1 | 1/2003 | Huter et al. | |
| 6,537,198 B1 | 3/2003 | Vidlund et al. | |
| 6,551,303 B1 | 4/2003 | Van Tassel et al. | |
| 6,592,608 B2 | 7/2003 | Fisher et al. | |
| 6,652,555 B1 | 11/2003 | VanTassel et al. | |
| 6,685,627 B2 | 2/2004 | Jayaraman | |
| 6,730,108 B2 | 5/2004 | Van Tassel et al. | |
| 6,776,754 B1 | 8/2004 | Wilk | |
| 6,852,076 B2 | 2/2005 | Nikolic et al. | |
| 6,959,711 B2 | 11/2005 | Murphy et al. | |
| 6,994,093 B2 | 2/2006 | Murphy et al. | |
| 7,144,363 B2 | 12/2006 | Pai et al. | |
| 7,279,007 B2 * | 10/2007 | Nikolic et al. | 623/11.11 |
| 7,303,526 B2 * | 12/2007 | Sharkey et al. | 600/37 |
| 2001/0014800 A1 | 8/2001 | Frazier et al. | |
| 2002/0019580 A1 | 2/2002 | Lau et al. | |
| 2002/0026092 A1 | 2/2002 | Buckberg et al. | |
| 2002/0028981 A1 | 3/2002 | Lau et al. | |
| 2002/0032481 A1 | 3/2002 | Gabbay | |
| 2002/0055767 A1 | 5/2002 | Forde et al. | |
| 2002/0055775 A1 | 5/2002 | Carpentier et al. | |
| 2002/0111647 A1 | 8/2002 | Khairkhahan et al. | |
| 2002/0133227 A1 | 9/2002 | Murphy et al. | |
| 2002/0161394 A1 | 10/2002 | Macoviak et al. | |
| 2002/0169359 A1 | 11/2002 | McCarthy et al. | |
| 2002/0169360 A1 | 11/2002 | Taylor et al. | |
| 2002/0188170 A1 | 12/2002 | Santamore et al. | |
| 2003/0045896 A1 | 3/2003 | Murphy et al. | |
| 2003/0050682 A1 | 3/2003 | Sharkey et al. | |
| 2003/0050685 A1 | 3/2003 | Nikolic et al. | |
| 2003/0105384 A1 * | 6/2003 | Sharkey et al. | 600/16 |
| 2003/0109770 A1 * | 6/2003 | Sharkey et al. | 600/16 |
| 2003/0120337 A1 | 6/2003 | Van Tassel et al. | |
| 2003/0149333 A1 | 8/2003 | Alferness | |
| 2003/0181942 A1 | 9/2003 | Sutton et al. | |
| 2003/0220667 A1 | 11/2003 | Van Der Burg et al. | |
| 2004/0002626 A1 | 1/2004 | Feld et al. | |
| 2004/0034366 A1 | 2/2004 | van der Burg et al. | |
| 2004/0044361 A1 | 3/2004 | Frazier et al. | |
| 2004/0064014 A1 | 4/2004 | Melvin et al. | |
| 2004/0127935 A1 | 7/2004 | VanTassel et al. | |
| 2004/0172042 A1 | 9/2004 | Suon et al. | |
| 2004/0260331 A1 | 12/2004 | D'Aquanni et al. | |
| 2004/0267378 A1 | 12/2004 | Gazi et al. | |
| 2005/0007031 A1 | 1/2005 | Hyder | |
| 2005/0015109 A1 | 1/2005 | Lichtenstein | |
| 2005/0085826 A1 | 4/2005 | Nair et al. | |
| 2005/0096498 A1 | 5/2005 | Houser et al. | |
| 2005/0113861 A1 | 5/2005 | Corcoran et al. | |
| 2005/0154252 A1 | 7/2005 | Sharkey et al. | |
| 2005/0177180 A1 | 8/2005 | Kaganov et al. | |
| 2005/0197716 A1 | 9/2005 | Sharkey et al. | |
| 2005/0216052 A1 | 9/2005 | Mazzocchi et al. | |
| 2005/0228434 A1 | 10/2005 | Amplatz et al. | |
| 2006/0025800 A1 | 2/2006 | Suresh | |
| 2006/0030881 A1 | 2/2006 | Sharkey et al. | |
| 2006/0276684 A1 | 12/2006 | Speziali | |
| 2009/0287040 A1 | 11/2009 | Khairkhahan et al. | |

FOREIGN PATENT DOCUMENTS

| | | |
|---|---|---|
| WO | WO 01/30266 | 5/2001 |
| WO | WO 01/78625 A1 | 10/2001 |
| WO | WO 02/30335 A2 | 4/2002 |

| WO | WO 02/071977 A2 | 9/2002 |
| WO | WO 03/007778 A | 1/2003 |
| WO | WO 03/073961 A1 | 9/2003 |
| WO | WO 2004/012629 A | 2/2004 |
| WO | WO 2004/047679 A1 | 6/2004 |
| WO | WO 2004/100803 | 11/2004 |
| WO | WO 2005/007031 | 1/2005 |

OTHER PUBLICATIONS

Khairkhahan, et al., U.S. Appl. No. 11/151,164, entitled "Peripheral seal for a ventricular partitioning device," filed Jun. 10, 2005.

Sharkey, et al., U.S. Appl. No. 11/199,633, entitled "Method for treating myocardial rupture," filed Aug. 9, 2005.

Khairkhahan, et al; U.S. Appl. No. 11/801,075, entitled "System for improving cardiac function," filed May 7, 2007.

Khairkhahan et al; U.S. Appl. No. 11/800,998, entitled "System for improving cardiac function," filed May 7, 2007.

Nikolic et al; U.S. Appl. No. 11/640,469, entitled "Cardiac device and methods of use thereof," filed Dec. 14, 2006.

Nikolic, et al., U.S. Appl. No. 12/129,443 entitled "Therapeutic methods and devices following myocardial infarction," filed May 29, 2008.

Khairkhahan et al; U.S. Appl. No. 12/125,015 entitled "Ventricular partitioning device," filed May 21, 2008.

Tetsuji Kawata et al., "Systolic and Diastolic Function After Patch Reconstruction of Left Ventricular Aneurysms", Ann. Thorac. Surg. 59, pp. 403-407, 1995.

Vincent Dor, "The Treatment of Refractory Ischemic Ventricular Tachycardia by Endoventricular Patch Plasty Reconstruction of the Left Ventricle", Seminars in Thoracic and Cardiovascular Surgery, vol. 9, No. 2, pp. 146-155, Apr. 1997.

Daniel Giorgio Di Mattia et al., "Surgical treatment of left ventricular post-infarction aneurysm with endoventriculoplasty: late clinical and functional results", European Journal of Cardio-thoracic Surgery 15, pp. 413-419, 1999.

T Katsumata et al., "An objective appraisal of partial left ventriculectomy for heart failure", Journal of Congestive Heart Failure and Circulator Support, pp. 97-106, 1999.

Vincent Dor, " Surgery for left ventricular aneurysm", Current Opinion in Cardiology, Current Science, pp. 773-780, 1990.

Vincent Dor et al., "Ventricular remodeling in coronary artery disease", Current Opinion in Cardiology, Rapid Science Publishers, pp. 533-537, 1997.

AGA Medical Corporation, www.amplatzer.com/products, "The Muscular VSD Occluder" and "The Septal Occluder" device descriptions, Apr. 3, 2002.

Gore Medical, www.goremedical.com, "Helex Septal Occluder" product description, Apr. 3, 2002.

Khairkhahan et al; U.S. Appl. No. 11/860,438 entitled "Laminar ventricular partitioning device," filed Sep. 24, 2007.

Khairkhahan et al; U.S. Appl. No. 12/198,010 entitled "Retrievable devices for improving cardiac function," filed Aug. 25, 2008.

Khairkhahan, Alexander; U.S. Appl. No. 12/181,282 entitled "Inflatable ventricular partitioning device," filed Jul. 28, 2008.

Khairkhahan et al; U.S. Appl. No. 12/198,022 entitled "Retrievable cardiac devices," filed Aug. 25, 2008.

Khairkhahan et al; U.S. Appl. No. 12/268,346 entitled "System for improving cardiac function," filed Nov. 10, 2008.

Khairkhahan et al; U.S. Appl. No. 12/422,177 entitled "Sealing and filling ventricular partitioning devices to improve cardiac function," filed Apr. 10, 2009.

* cited by examiner

MULTIPLE PARTITIONING DEVICES FOR HEART TREATMENT

RELATED APPLICATIONS

This application is a continuation-in-part of application Ser. No. 10/302,269, filed on Nov. 22, 2002 now abandoned, which is incorporated herein by reference. This application is also a continuation-in-part of application Ser. No. 10/212,033, filed on Aug. 1, 2002, now U.S. Pat. No. 7,303,526.

FIELD OF THE INVENTION

The present invention relates generally to the treatment of a patient's heart, particularly congestive heart failure by partitioning a chamber of the patient's heart.

BACKGROUND OF THE INVENTION

Congestive heart failure (CHF) is characterized by a progressive enlargement of the heart, particularly the left ventricle and is a major cause of death and disability in the United States. Approximately 550,000 new cases occur annually in the U.S. alone. As the patient's heart enlarges, it cannot efficiently pump blood forward with each heart beat. In time, the heart becomes so enlarged the heart becomes ineffective as a pump and cannot adequately supply blood to the body. Even in healthy hearts only a certain percentage of the blood in a patient's left ventricle is pumped out or ejected from the chamber during each stroke of the heart. The pumped percentage, commonly referred to as the "ejection fraction", is typically about sixty percent for a healthy heart. A patient with congestive heart failure can have an ejection fraction of less than 40% and sometimes much lower. As a result of the low ejection fraction, a patient with congestive heart failure is fatigued, unable to perform even simple tasks requiring exertion and experiences shortness of breath and discomfort. Further, as the heart enlarges, the internal heart valves such as the mitral valve cannot adequately close. An incompetent mitral valve allows regurgitation of blood from the left ventricle back into the left atrium, further reducing the heart's ability to pump blood forwardly.

Congestive heart failure can result from a variety of conditions, including viral infections, incompetent heart valves (e.g. mitral valve), ischemic conditions in the heart wall or a combination of these conditions. Prolonged ischemia and occlusion of coronary arteries can result in a portion of the ventricular wall dying and becoming scar tissue. Once the myocardial tissue dies, it is less contractile (sometimes non-contractile) and no longer contributes to the pumping action of the heart. It is referred to as hypokinetic or akinetic. As the disease progresses, a local area of compromised myocardium may bulge out during the heart contractions, further decreasing the heart's ability to pump blood and further reducing the ejection fraction. In this instance, the heart wall is referred to as dyskinetic. The dyskinetic region of the heart wall may stretch and eventually form an aneurysmic bulge.

Patients suffering from congestive heart failure are commonly grouped into four classes, Classes I, II, III and IV. In the early stages, Classes I and II, drug therapy is presently the most common treatment. Drug therapy typically treats the symptoms of the disease and may slow the progression of the disease, but it can not cure the disease. Presently, the only permanent treatment for congestive heart disease is heart transplantation, but heart transplant procedures are very risky, extremely invasive and expensive and are performed on a small percentage of patients. Many patient's do not qualify for heart transplant for failure to meet any one of a number of qualifying criteria, and, furthermore, there are not enough hearts available for transplant to meet the needs of CHF patients who do qualify.

Substantial effort has been made to find alternative treatments for congestive heart disease. For example, surgical procedures have been developed to dissect and remove weakened portions of the ventricular wall in order to reduce heart volume. This procedure is highly invasive, risky and expensive and is commonly only done in conjunction with other procedures (such as heart valve replacement or coronary artery by-pass graft). Additionally, the surgical treatment is usually only offered to Class III and IV patients and, accordingly, is not an option for most patients facing ineffective drug treatment. Finally, if the procedure fails, emergency heart transplant is the only presently available option.

Mechanical assist devices have been developed as intermediate procedures for treating congestive heart disease. Such devices include left ventricular assist devices and total artificial hearts. A left ventricular assist device includes a mechanical pump for increasing blood flow from the left ventricle into the aorta. Total artificial heart devices, such as the Jarvik heart, are usually used only as temporary measures while a patient awaits a donor heart for transplant.

Recently, improvements have been made in treating patient's with CHF by implanting pacing leads in both sides of the heart in order to coordinate the contraction of both ventricles of the heart. This technique has been shown to improve hemodynamic performance and can result in increased ejection fraction from the right ventricle to the patient's lungs and the ejection fraction from the left ventricle to the patient's aorta. While this procedure has been found to be successful in providing some relief from CHF symptoms and slowed the progression of the disease, it has not been able to stop the disease and is only indicated in patients with ventricular dissynchrony.

Other efforts to treat CHF include the use of an elastic support, such as an artificial elastic sock, placed around the heart to prevent further deleterious remodeling.

SUMMARY OF THE INVENTION

The present invention is directed to a method and system for using a plurality of ventricular partitioning devices in the treatment of a patient's heart for disorders such as congestive heart failure (CHF). Specifically, the multiple devices are deployed within a patient's heart chamber so as to partition the heart chamber into a main productive portion and a secondary non-productive portion as described in copending application Ser. No. 10/913,608, filed on Aug. 5, 2004. This partitioning reduces the total volume of the heart chamber, reduces the stress applied to the heart and, as a result, improves the ejection fraction and blood flow thereof. Multiple partitioning devices are deployed when one partitioning device is of a size or shape which is insufficient to cover damaged heart tissue within the heart wall defining the chamber to be partitioned.

One first partitioning device embodying features of the invention has a reinforced partitioning component with a pressure receiving surface which defines in part the main productive portion of the partitioned heart chamber when secured within the patient's heart chamber and a distally depending support member for engaging a region of the patient's heart wall defining in part the non-productive portion of the chamber of the partitioned heart. A suitable first partitioning device is described in copending application Ser. No. 10/913,608, filed on Aug. 5, 2004, and Ser. No. 11/151, 164 filed Jun. 10, 2006.

The second partitioning device is similar to the first but is configured to fit over and preferably off-set from the first partitioning device to cover damaged areas of the patient's heart wall that may not be effectively covered by the first partitioning device. The second partitioning device embodying features of the invention is similar to the first partitioning device and has a reinforced partitioning component with a pressure receiving surface which helps partition the heart chamber into the main productive portion and non-productive portion when secured within the patient's heart chamber. The second partitioning device may be an independent device, may be tethered or otherwise connected or secured to the first partitioning device, or may be secured to the first partitioning device when deployed.

The first and second partitioning devices preferably have a reinforced membrane that forms the pressure receiving surface. The membranes of the devices are reinforced by a radially expandable frame component formed of a plurality of ribs. The ribs of the expandable frames have distal ends secured to central hubs and the free proximal ends thereof configured to engage and preferably penetrate tissue of the heart wall. The secured distal ends of the ribs are preferably configured to facilitate radial self expansion of the free proximal ends of the ribs away from a centerline axis upon deployment within the heart chamber. The distal ends of the ribs may be biased outwardly or fixed to the hub and formed of material such as superelastic NiTi alloy which allows for compressing the free proximal ends of the ribs toward a centerline axis into a contracted configuration for delivery through a delivery catheter and, when released from the compression within the delivery catheter after deployment within the patient's heart chamber, allow for their self expansion to an expanded configuration within the chamber. Alternative designs such as described in applications referred to herein may be employed.

The free proximal ends of the ribs are configured to engage and preferably penetrate the tissue lining the heart chamber to be partitioned so as to secure the peripheral edges of the partitioning devices to the heart wall and fix the partitioning component within the chamber so as to partition the chamber in a desired manner. The tissue penetrating proximal tips are configured to penetrate the tissue lining at an angle approximately perpendicular to a center line axis of the partitioning device (e.g. ±30° from a line perpendicular to the center line axis). The tissue penetrating proximal tips of the ribs may be provided with barbs, hooks and the like which anchor the tips within the heart wall and prevent their withdrawal.

The ribs in their expanded configuration angle outwardly from the hub and the free proximal ends curve outwardly so that the membrane secured to the ribs of the expanded frame forms a trumpet-shaped, pressure receiving surface.

The partitioning membrane in the expanded configuration has radial dimensions from about 10 to about 160 mm, preferably about 50 to about 100 mm, as measured from the center line axis.

The partitioning device may be delivered percutaneously or intraoperatively. Suitable delivery catheters are described in copending application Ser. No. 10/913,608, filed on Aug. 5, 2004, and Ser. No. 11/151,164 filed Jun. 10, 2005.

The partitioning devices embodying features of the invention are relatively easy to install and they substantially improve the pumping action of the heart and provide an increase in the ejection fraction of the patient's heart chamber. These and other advantages of the invention will become more apparent from the following detailed description of the invention and the accompanying exemplary drawings.

DETAILED DESCRIPTION OF EMBODIMENTS OF THE INVENTION

Figure 1:
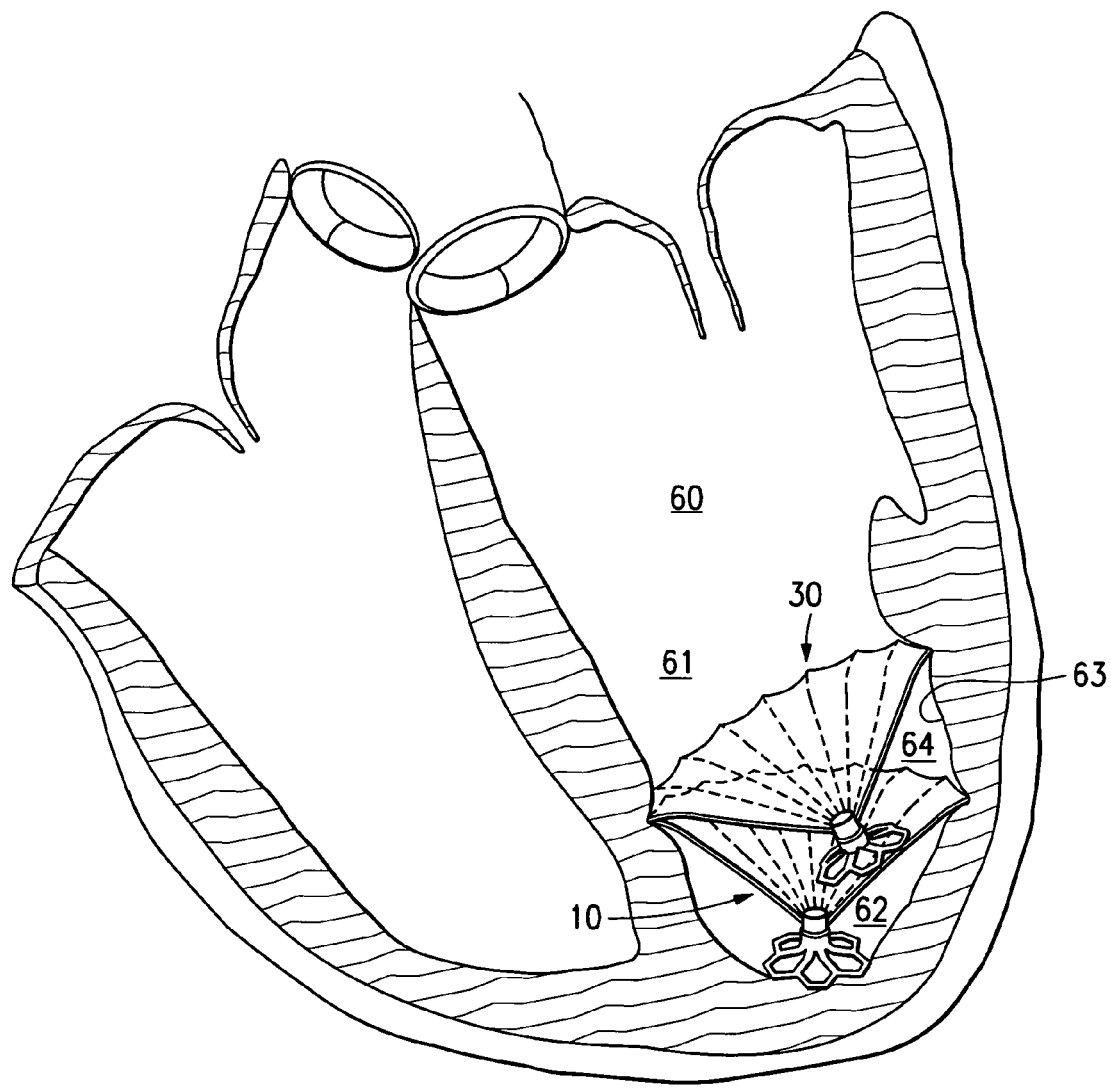
FIG. 1 is an elevational view of multiple partitioning devices embodying features of the invention deployed within a patient's left ventricle.

FIG. 1 illustrates a pair of partitioning devices 10 and 30 which are secured within a patient's heart chamber 60 (left ventricle) to partition the heart chamber into a productive portion 61 and a non-productive portion 62. The first partitioning device 10 is deployed at the apex of the heart chamber 60 and the second partitioning device 30 is deployed on top of the first device at a slight angle with respect to the first partitioning device to cover a damaged or weakened region 63 of the heart wall and define at least in part an additional non-productive portion 64 of the patient's heart chamber. In FIG. 1 the first and second partitioning devices 10 and 30 have essentially the same design and are independent from each other. The physician or other operating personnel may determine before or during the partitioning procedure that the first partitioning device 10 by itself will not adequately partition the heart chamber 60 and that a second partitioning device 30 may be needed to more completely partition the heart chamber as shown in FIG. 1. The second partitioning device 30 has essentially the same structure as the first partitioning device 10, except that the radial dimensions of the second partitioning device 30 is usually greater than the radial dimensions of the first partitioning device.

Figure 2:
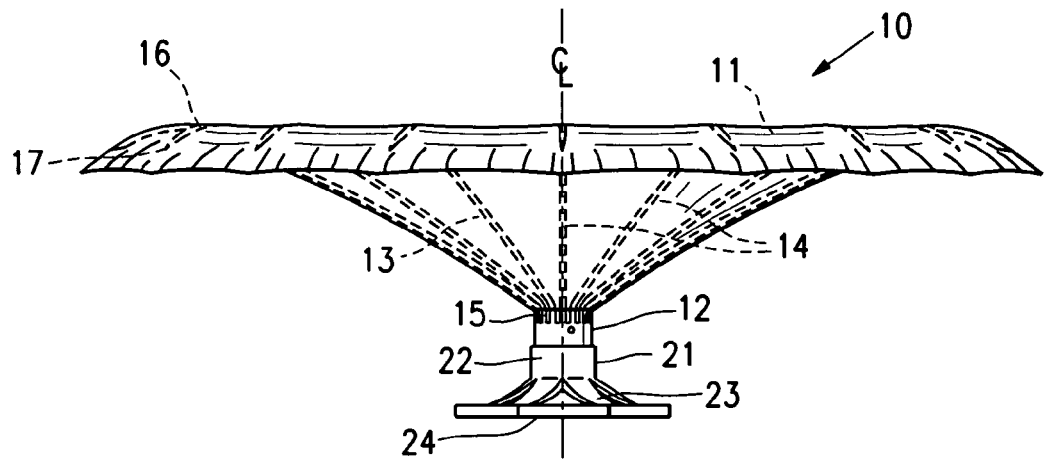
FIG. 2 is an elevational view of the first partitioning device shown in FIG. 1.

FIGS. 2-7 illustrate details of the first partitioning device 10 (and partitioning device 30 which has essentially the same construction) which includes a partitioning membrane 11, a hub 12, preferably centrally located on the partitioning device, and a radially expandable reinforcing frame 13 formed of a plurality of ribs 14. Preferably, the partitioning membrane 11 is secured to the proximal or pressure side of the frame 13 as shown in FIG. 2. The ribs 14 have distal ends 15 which are secured to the hub 12 and free proximal ends 16 which are configured to curve or flare away from a center line axis. Radial expansion of the free proximal ends 16 unfurls the membrane 11 secured to the frame 13 so that the membrane defines in part the productive portion of the patient's partitioned heart chamber 60.

Figure 6:
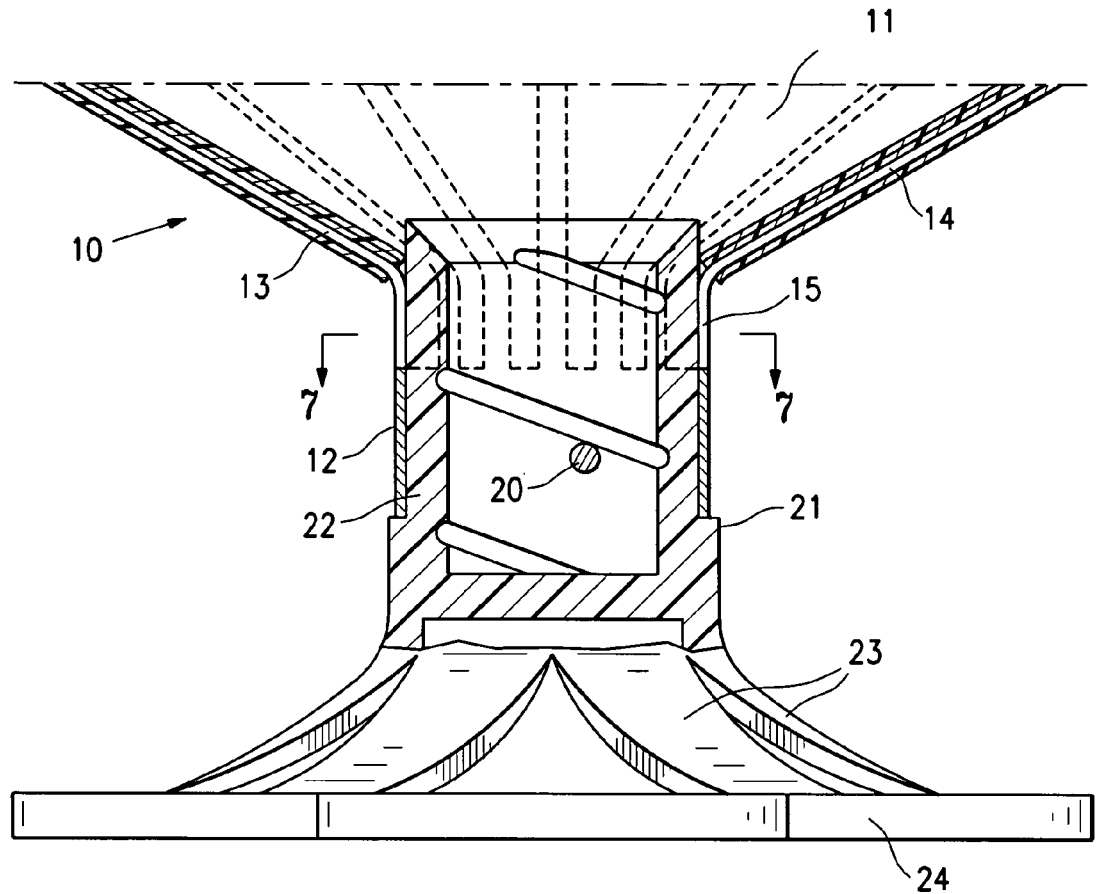
FIG. 6 is a partial cross-sectional view of the hub of the partitioning device shown in FIG. 3 taken along the lines 6-6.
Figure 7:
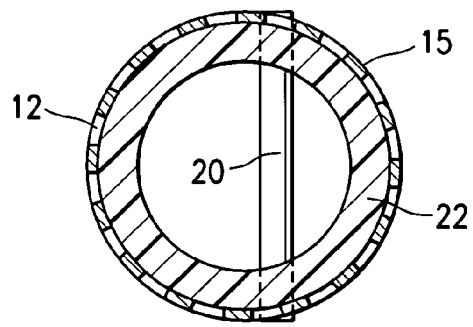
FIG. 7 is a transverse cross sectional view of the hub shown in FIG. 6 taken along the lines 7-7.

As shown in more detail in FIGS. 6 and 7, the distal ends 15 of the ribs 14 are secured within the hub 12 and a transversely disposed connector bar 20 to the non-traumatic support component 21 and thus the partitioning component 10 to delivery systems such as shown in copending application Ser. No. 10/913,608, filed on Aug. 5, 2004, and Ser. No. 11/151,164 filed Jun. 10, 2005. The curved free proximal ends 16 of ribs 14 are provided with sharp tip elements 17 which are configured to hold the frame 13 and the membrane 11 secured thereto in a deployed position within the patient's heart chamber. Preferably, the sharp tip elements 17 of the frame 13 penetrate into tissue of the patient's heart wall in order to secure the partitioning component 10 within the heart chamber so as to partition the ventricular chamber into a productive portion and a non-productive portion.

Figure 3:
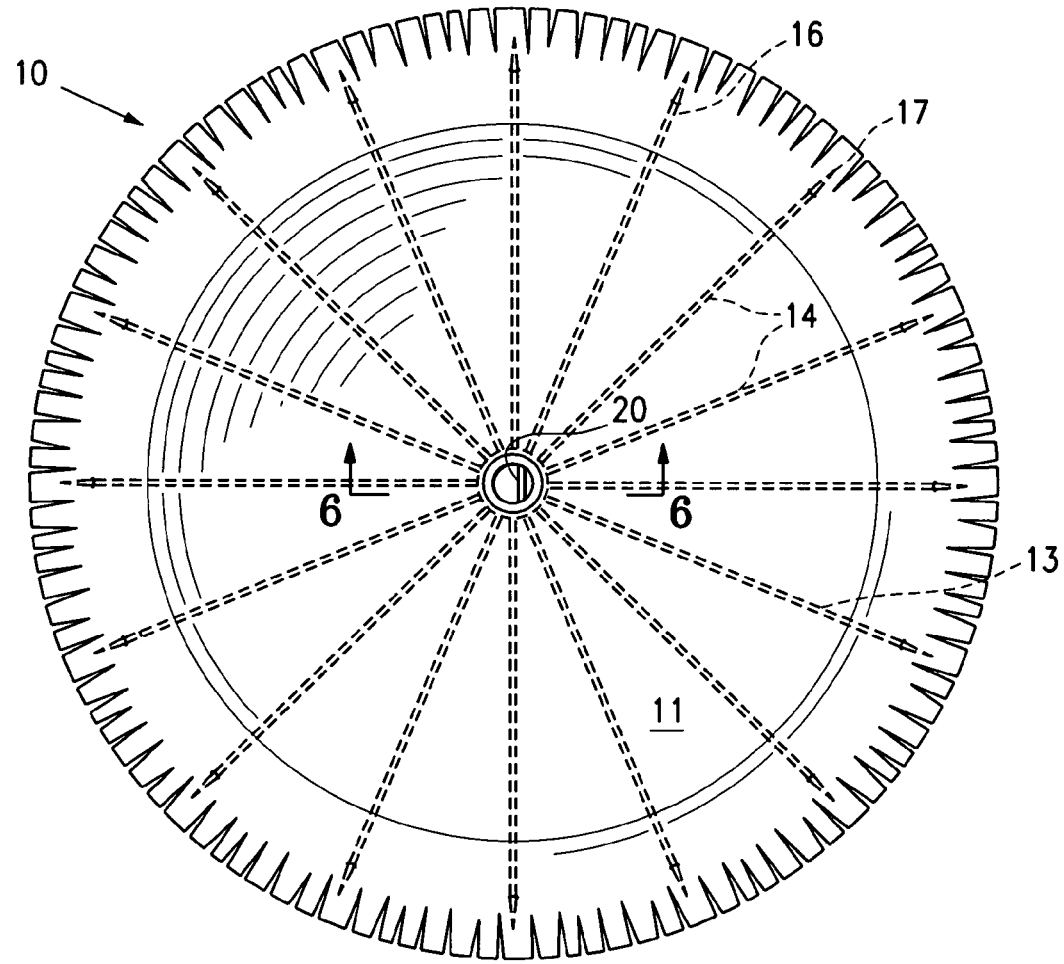
FIG. 3 is a plan view of the partitioning device shown in FIG. 2 illustrating the upper surface of the device.
Figure 4:
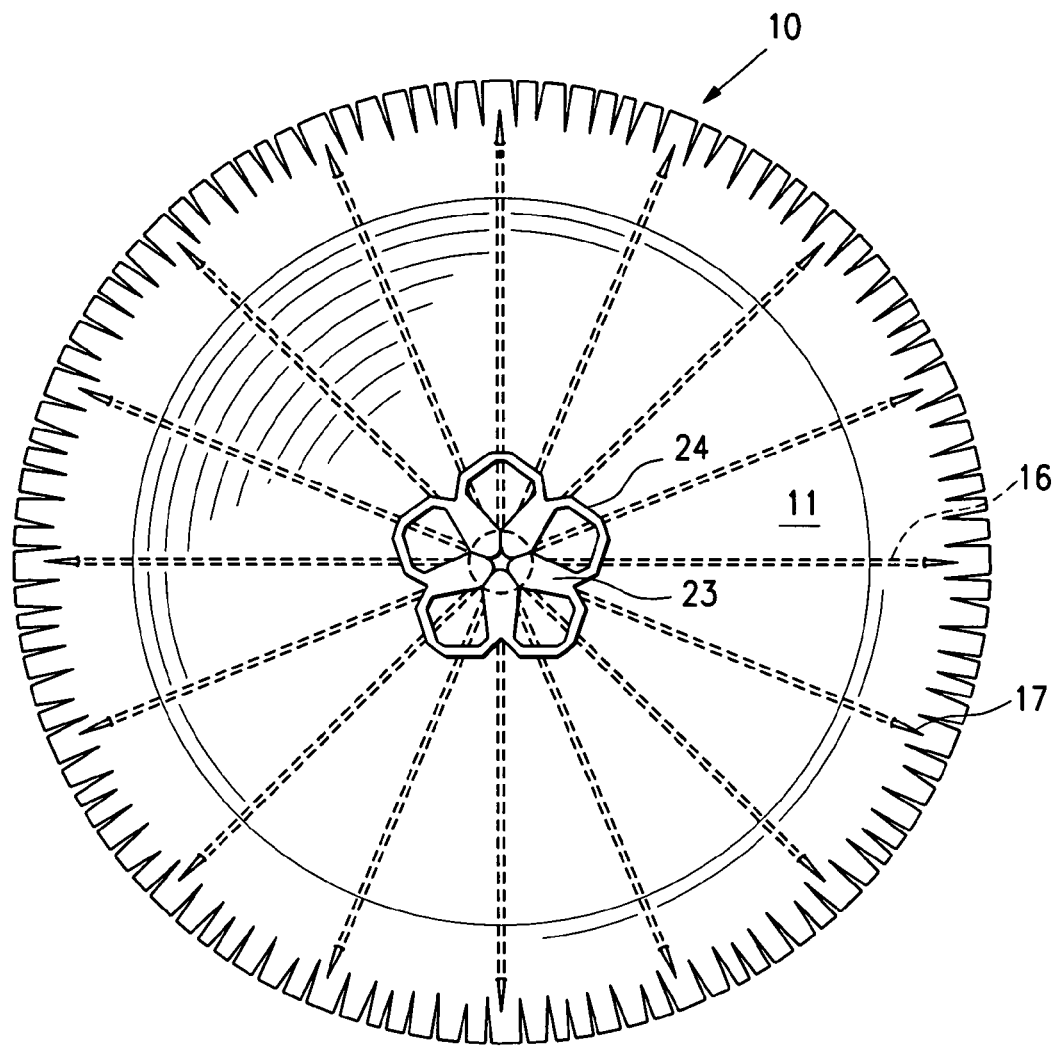
FIG. 4 is bottom view of the partitioning device shown in FIG. 2.
Figure 5:
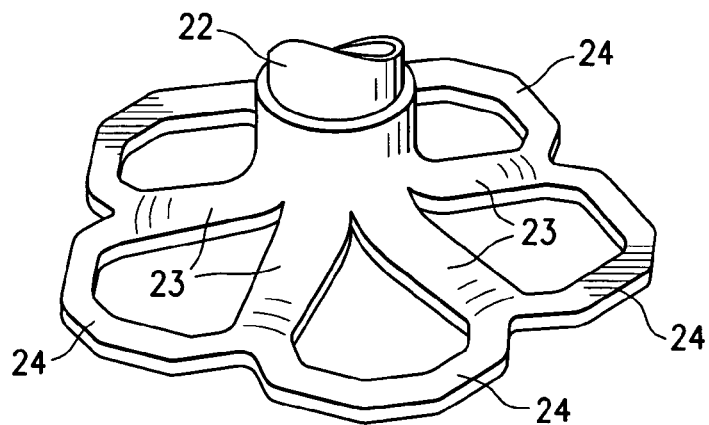
FIG. 5 is a perspective view of the non-traumatic tip of the distally extending stem of the device shown in FIG. 2.

The connector bar 20 of the hub 12 allows the partitioning device 10 to be secured to the non-traumatic component 21 which can be secured to a delivery system for delivery and to be released from the delivery system within the patient's heart chamber for deployment. The distal ends 15 of the reinforcing ribs 14 are secured within the hub 12 in a suitable manner or they may be secured to the surface defining the inner lumen or they may be disposed within channels or bores in the wall of the hub 12. The ribs 14 are preshaped so that when not constrained other than by the membrane 11 secured thereto (as shown in FIGS. 2 and 3), the free proximal ends 16 thereof expand to a desired angular displacement away from a center line axis which is about 20° to about 90°, preferably about 50° to about 80°.

A non-traumatic support component 21 is secured to the hub 12 and has a stem 22 and a plurality of feet or pods 23 extending radially away from the center line axis. The ends of the feet 23 are secured to struts 24 which extend between adjacent feet. A plane of material (not shown) may extend between adjacent feet 23 in a web-like fashion to provide further support in addition to or in lieu of the struts 24. The inner diameter of the stem 22 is threaded to secure the partitioning device 10 to a delivery catheter as disclosed in previously discussed copending application Ser. No. 10/913,608 and application Ser. No. 11/151,164.

Figure 8:
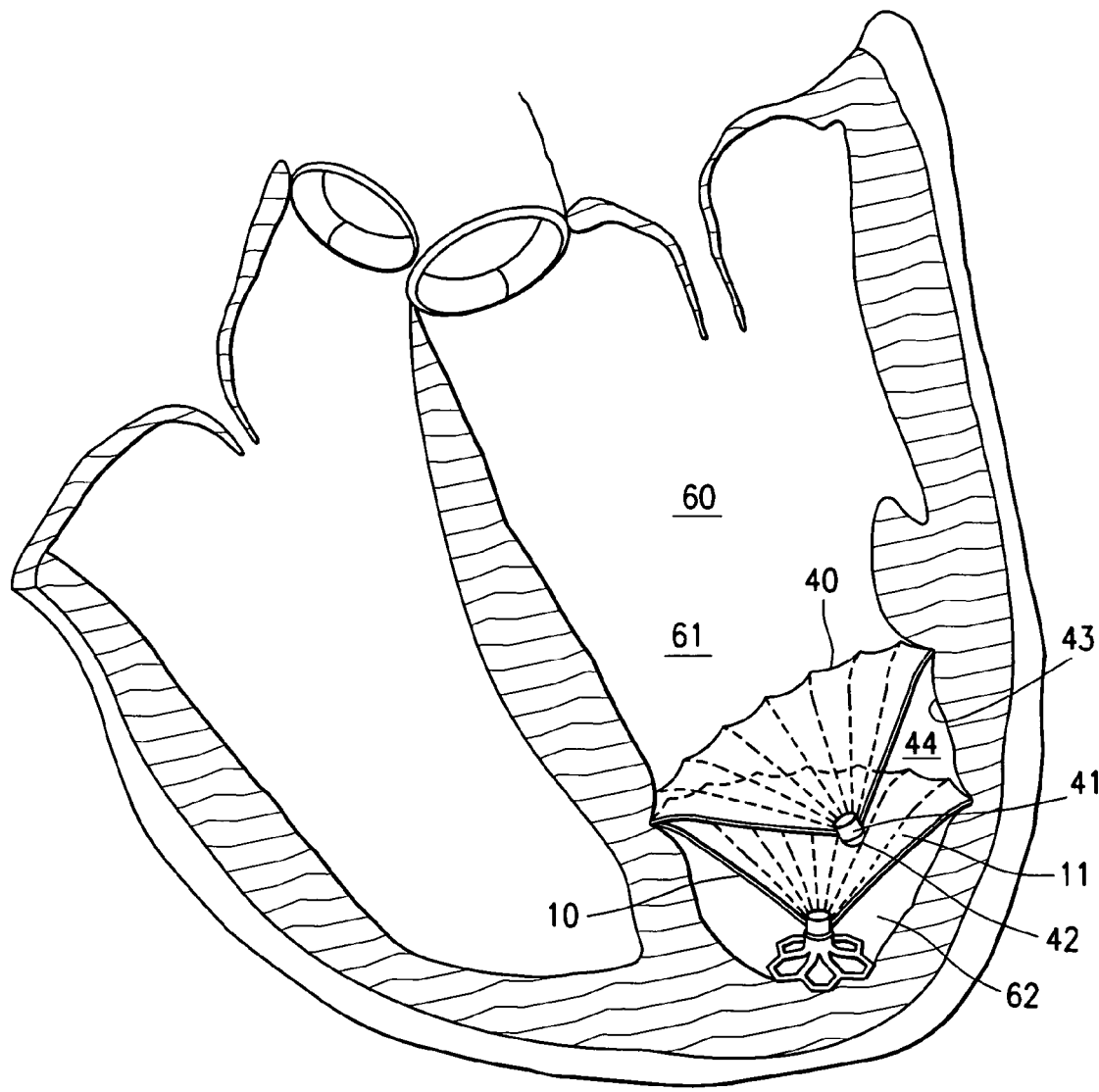
FIG. 8 is an elevational view of a pair of partitioning devices deployed within a patient's heart chamber with the second partitioning device being of an alternative design.

FIG. 8, similar to FIG. 1, illustrates the deployment of the first partitioning device 10 and an alternative second partitioning device 40 within a patient's heart chamber. The alternative second partitioning device 40 has a shortened support component 41 which has a rounded distal tip 42. It has no stem or a shortened stem with no feet as shown with the second partitioning device 30 shown in FIG. 1. The second partitioning device 40 covers additional region 43 of the heart wall and defines in part non-productive portion 44 of the heart chamber 60.

Figure 9:
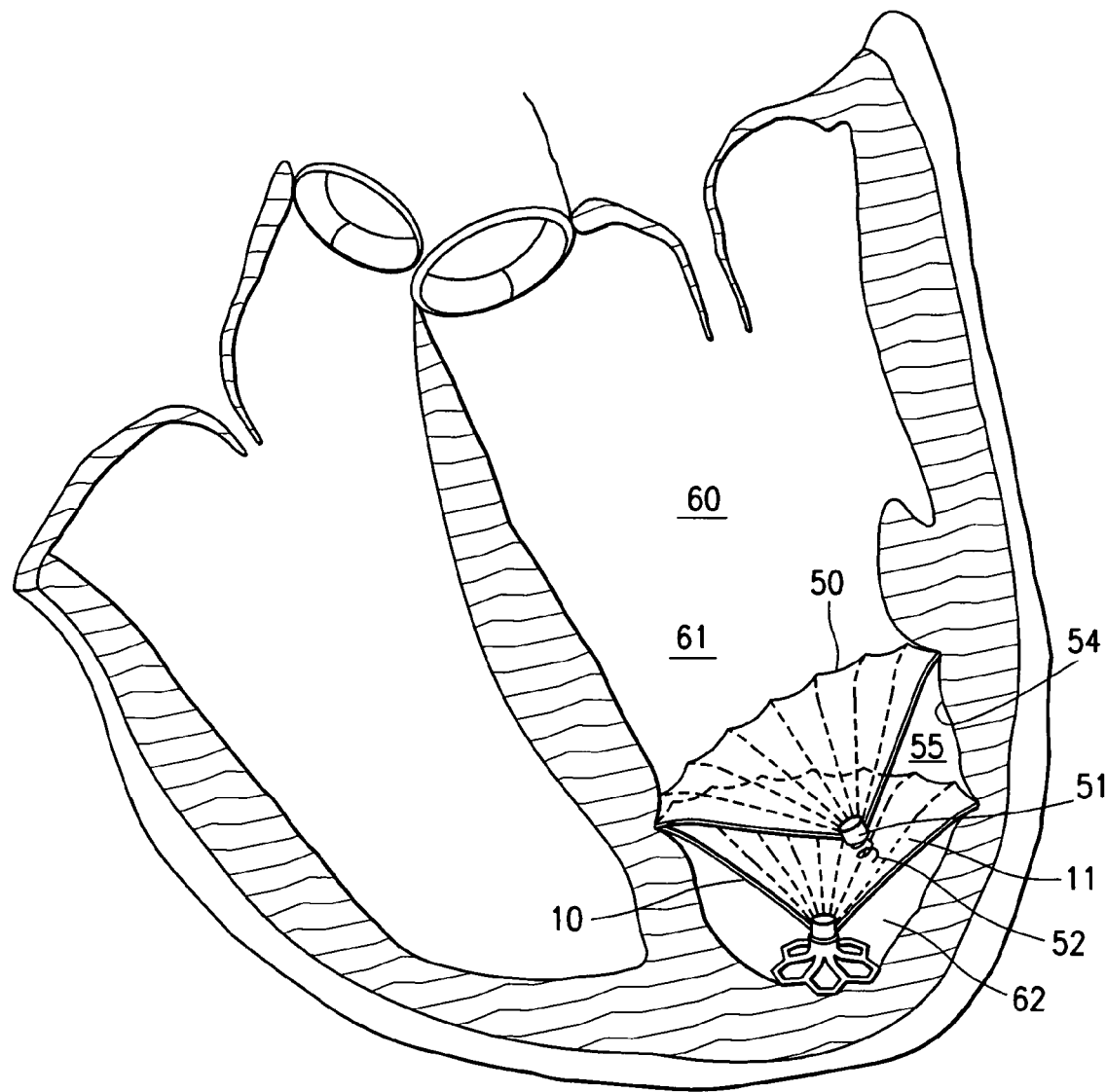
FIG. 9 is an elevational view of a pair of partitioning devices deployed within a patient's heart chamber with the second partitioning device being of another alternative design.

FIG. 9, similar to FIGS. 1 and 8 illustrates the deployment of the first partitioning device 10 and another second alternative partitioning device 50. The second alternative partitioning device 50 has a support component 51 configured to extend through an aperture (not shown) in the membrane 11 of the first partitioning device 10. The support component 51 has a helical coil 52 to facilitate securing the second partitioning device 50 to a region of the membrane 11 or a rib 14 of the first partitioning device 10. The second alternative partitioning device 50 covers region 54 of the heart wall and defines in part non-productive portion 55 of the heart chamber 60.

Figure 10:
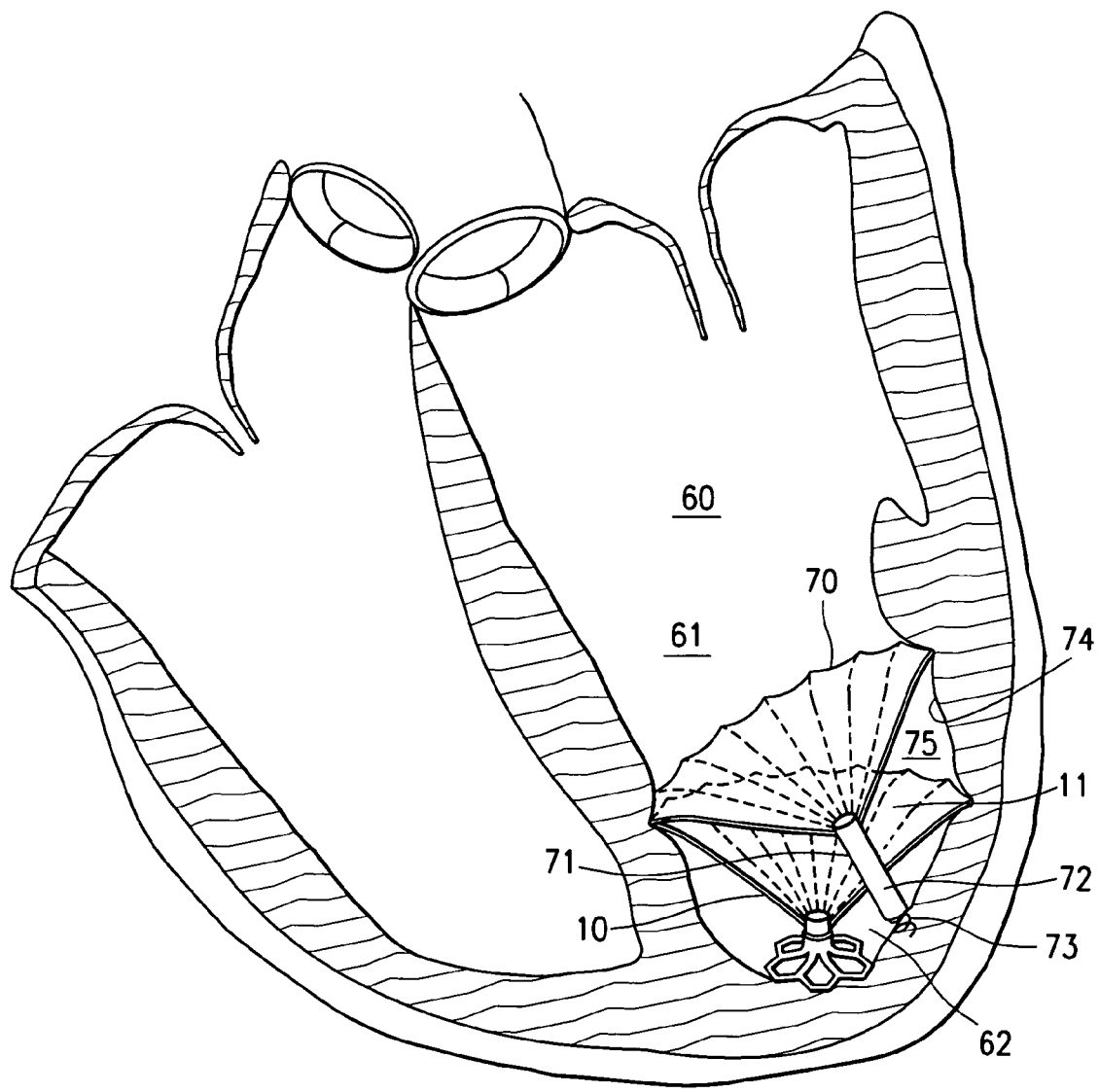
FIG. 10 is an elevational view of a pair of partitioning devices deployed within a patient's heart chamber with the second partitioning device being of another alternative design.

FIG. 10, similar to FIG. 9, illustrates the deployment of the first partitioning device 10 and another alternative second partitioning device 70. The alternative second partitioning device 70 has a support component 71 with a distally depending support stem 72 with a helical coil 73 on the distal end of the stem to facilitate attachment of the stem to an underlying region of the patient's heart wall. The stem passes through an aperture (not shown) provided in the membrane 11 of the first partitioning device 10. This arrangement also allows the deployment of the second partitioning device 70 off-set from the first partitioning device 10 to cover a greater region 74 of the patient's heart wall and define in part non-productive portion 75 of the heart chamber 60.

Figure 11:
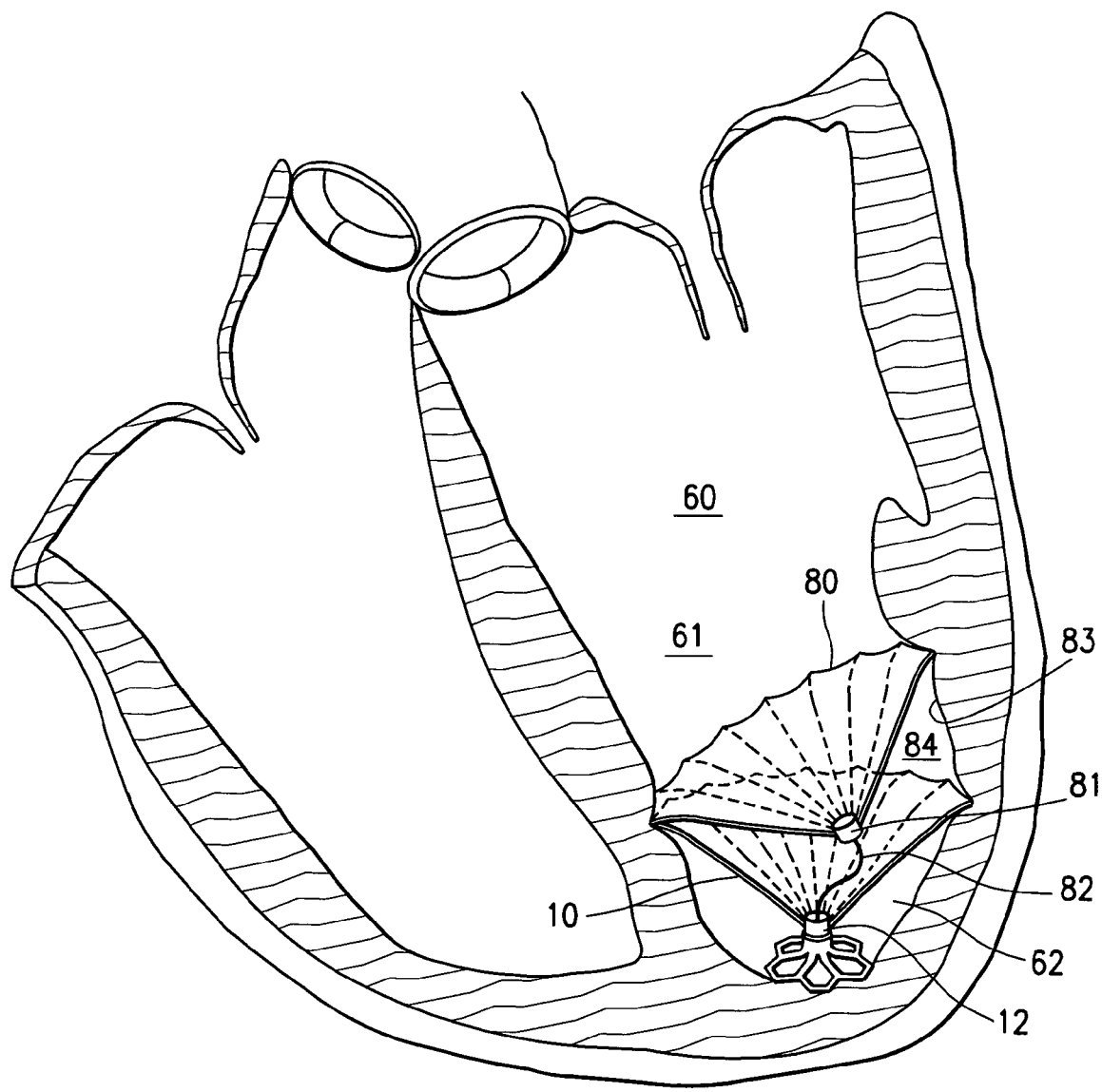
FIG. 11 is an elevational view of a pair of partitioning devices deployed within a patient's heart chamber with the second partitioning device being of another alternative design with a tether or strand connecting the hub of the second partitioning device to the hub of the first partitioning device.
Figure 12:
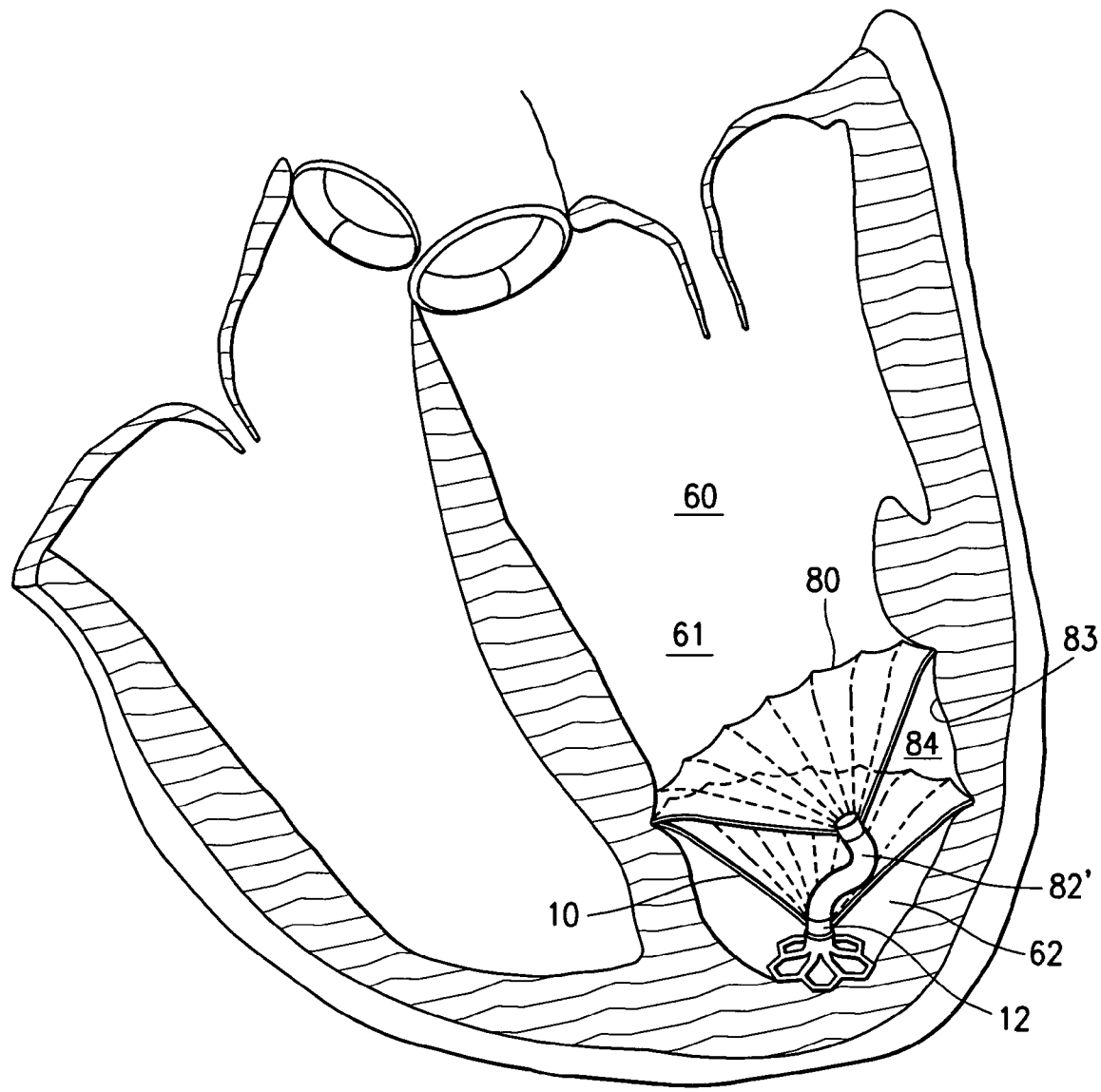
FIG. 12 is an elevational view of a pair of partitioning devices deployed within a patient's heart chamber with the hub of the second partitioning device being connected to the hub of the first partitioning device by a tubular member.

FIG. 11 illustrates deployment of the first partitioning device 10 and another alternative second partitioning device 80 which has a support component 81 similar to that shown in FIG. 9 but with an elongated tether or strand 82 which has one end secured to the support component 81 and extends to and is secured to the hub 12 of the partitioning device 10. The tether or strand 82 may be formed of a suitable biocompatible polymeric fabric. Strand 82 may also be in the form of a helical coil and have a bias to maintain the length of the tether extending between the first and second partitioning devices. The second partitioning device 80 covers region 83 of the patient's heart wall and defines in part non-production portion 84 of the heart chamber 60. Alternatively, a tether 82' extending between the first and second partitioning devices may be in the form of a tubular element as shown in FIG. 12.

Over time, the non-productive portions 44, 55, 62, 75 and 84 of the heart chamber 60 fill first with thrombus and subsequently with cellular growth. Bio-resorbable fillers such as polylactic acid, polyglycolic acid, polycaprolactone and copolymers and blends may be employed to initially fill the non-productive portions. Other materials which accelerate tissue growth or thrombus may be deployed in the non-productive portions.

The partitioning devices may be conveniently formed by the methods described in previously discussed copending application Ser. No. 10/913,608.

While porous ePTFE material is preferred membrane material, the membrane 11 may be formed of suitable biocompatible polymeric material which include Nylon, PET (polyethylene terephthalate) and polyesters such as Hytrel. The membrane 11 is preferably foraminous in nature to facilitate tissue ingrowth after deployment within the patient's heart.

To the extent not otherwise described herein, the various components of the partitioning devices may be formed of conventional materials and in a conventional manner as will be appreciated by those skilled in the art.

While particular forms of the invention have been illustrated and described herein, it will be apparent that various modifications and improvements can be made to the invention. Moreover, individual features of embodiments of the invention may be shown in some drawings and not in others, but those skilled in the art will recognize that individual features of one embodiment of the invention can be combined with any or all the features of another embodiment. Accordingly, it is not intended that the invention be limited to the specific embodiments illustrated. It is intended that this invention to be defined by the scope of the appended claims as broadly as the prior art will permit.

Terms such a "element", "member", "component", "device", "section", "portion", "step", "means" and words of similar import, when used herein shall not be construed as invoking the provisions of 35 U.S.C. §112(6) unless the following claims expressly use the terms "means" followed by a particular function without specific structure or "step" followed by a particular function without specific action. Accordingly, it is not intended that the invention be limited, except as by the appended claims. All patents and patent applications referred to above are hereby incorporated by reference in their entirety.

What is claimed is:

1. A method of treating a patient's heart by partitioning a chamber of the patient's heart into functioning and non-functioning portions, comprising:
   a. providing a first partitioning component which has an expandable reinforced membrane having a pressure receiving face in an expanded, deployed configuration;
   b. providing a second partitioning component having a second partitioning component which has an expandable reinforced membrane having a pressure receiving face in an expanded deployed configuration;
   c. deploying the first partitioning component in a partially expanded configuration within the chamber of the patient's heart to form in part a primary productive portion of the patient's heart chamber;
   d. securing the periphery of the reinforced membrane of the first partitioning component to the patient's heart wall;
   e. deploying the second partitioning component in a partially expanded configuration within the chamber of the patient's heart to cover a region of the patient's heart wall which is not covered by the first partitioning component to form in part the primary productive portion of the patient's heart chamber;
   f. securing the periphery of the reinforced membrane of the second partitioning component to the patient's heart wall.

2. The method of claim 1 wherein the distal tip of the support stem of the second component is passed through the membrane of the first partitioning.

3. The method of claim 2 wherein the distal tip of the support stem of the second partitioning device is secured to a rib of the reinforced membrane of the first partitioning component.

4. The method of claim 1 wherein the distal tip of the support stem of the second partitioning component is secured to a section of the patient's heart wall which is covered by the reinforced membrane of the first partitioning component.

5. The method of claim 1 wherein the support component of the second partitioning device is secured to the first partitioning device by a tether or strand.

6. The method of claim 1, wherein the second partitioning component has an expandable reinforced membrane having a pressure receiving face in an expanded deployed configuration with larger dimensions than the pressure receiving face of the first reinforced membrane.

7. A method for treating a patient's heart by partitioning a chamber of the patient's heart into functioning and non-functioning portions, comprising:
   a. the step for providing a first partitioning device which has an expandable reinforced membrane having a pressure receiving face in an expanded, deployed configuration;
   b. the step for providing a second partitioning device which has an expandable reinforced membrane having a pressure receiving face in an expanded deployed configuration;
   c. the step for deploying the first partitioning device in a partially expanded configuration within the chamber of the patient's heart to form in part a primary productive portion of the patient's heart chamber;
   d. the step for securing the periphery of the reinforced membrane of the first partitioning device to the patient's heart wall;
   e. the step for deploying the second partitioning device in a partially expanded configuration within the chamber of the patient's heart to cover a region of the patient's heart wall which is not covered by the first partitioning device to form in part the primary productive portion of the patient's heart chamber; and
   f. the step for securing the periphery of the reinforced membrane of the second partitioning component to the patient's heart wall.

* * * * *